(12) United States Patent
Jeunehomme et al.

(10) Patent No.: US 7,548,640 B2
(45) Date of Patent: Jun. 16, 2009

(54) METHOD AND APPARATUS FOR CALIBRATION AND CORRECTION OF GRAY LEVELS IN IMAGES

(75) Inventors: Fanny Jeunehomme, Versailles (FR); Serge Muller, Guyancourt (FR); Razvan Iordache, Paris (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/115,596

(22) Filed: May 6, 2008

(65) Prior Publication Data

US 2008/0205738 A1  Aug. 28, 2008

Related U.S. Application Data

(63) Continuation of application No. 10/775,912, filed on Feb. 10, 2004, now abandoned.

(30) Foreign Application Priority Data

Feb. 14, 2003  (FR)  .................................... 03 01797

(51) Int. Cl.
*G06K 9/00* (2006.01)
(52) U.S. Cl. ....................... 382/132; 382/169
(58) Field of Classification Search .................. None
See application file for complete search history.

(56) References Cited

U.S. PATENT DOCUMENTS 4,975,935 A   12/1990   Hillen et al.

(Continued)

FOREIGN PATENT DOCUMENTS

EP   0 564 182 A   10/1996
FR   2622714 A   5/1989

OTHER PUBLICATIONS

Siewerden et al. "A Ghost Story: Spatio-Temporal Response Characteristics of an Indirect-Detection Flat-Panel Imager", Med. Phys. v. 26, No. 8, Aug. 1999, pp. 1624-1641.

(Continued)

*Primary Examiner*—Matthew C Bella
*Assistant Examiner*—Claire Wang
(74) *Attorney, Agent, or Firm*—GE Global Patent Operation (57) ABSTRACT

A method and apparatus for calibrating an apparatus that acquires a sequence of radiographic images and correcting images of an object under observation. For each image of a sequence acquired by the apparatus and for a given frequency of acquisition of the sequence, the apparatus is calibrated by determining the value of the variation of a mean of gray levels in at least one zone of interest of the current image of at least one calibration device, the variation being determined relative to the mean gray level of the first image of the sequence in each zone of interest. The determination of the variation is reiterated for a series of images sequences acquired using calibration devices resulting in first images of mean gray levels different from one sequence to another. Each image of an image sequence of the object under observation is corrected, comprising zones of observation having different gray levels by subtracting from the current image the variation of one gray level relative to the first image of the object, the subtraction being a function of the gray level considered from each zone of observation.

10 Claims, 6 Drawing Sheets

U.S. PATENT DOCUMENTS

| | | |
|---|---|---|
| 5,452,338 A | 9/1995 | Granfors et al. |
| 5,923,722 A | 7/1999 | Schulz |
| 6,201,850 B1 | 3/2001 | Heumann |
| 6,694,047 B1 | 2/2004 | Farrokhnia et al. |
| 7,027,650 B2 * | 4/2006 | Williame et al. ............ 382/215 |

OTHER PUBLICATIONS

Pourjavid et al., "Compensation for Image Retintion in an Amorphous Silicon Detector", Proc. SPIE, v.2, No. 3659, Feb. 21, 1999, pp. 501-509.

* cited by examiner

METHOD AND APPARATUS FOR CALIBRATION AND CORRECTION OF GRAY LEVELS IN IMAGES

CROSS-REFERENCE TO RELATED APPLICATIONS

This application is a continuation of U.S. application Ser. No. 10/775,912 filed Feb. 10, 2004 which claims priority under 35 USC 119(a)-(d) to French Patent Application No. 03 01797 filed Feb. 14, 2003, the entire contents of which are hereby incorporated by reference.

BACKGROUND OF THE INVENTION

The present invention relates to a method apparatus for calibrating and correction of gray levels in images. In particular, the present invention is directed to acquiring a sequence of radiographic images and correction images of an object under observation. More particularly, the present invention relates to a method and apparatus for an acquiring sequence of radiographic images and calibration and correction of images of an object under observation by subtracting from each image of the sequence the spurious variation of a gray level between the images of the same sequence. The present invention can be particularly used in the medical field, such as, for example, in mammography and in the detection of cancerous tumors.

A known radiographic apparatus is comprises a console, means for providing a beam of radiation in the direction of means for detection. The means for detecting receives the radiation after passing through an object under observation placed in the observation space arranged in the beam, between on the means for providing the beam of radiation and on the means for detection. The known apparatus also comprises means for processing enabling acquiring and processing a sequence of images of an object sent from the means for detection.

The difference in absorption of the radiation by the different parts of the object under observation enables obtaining information on the composition of the object. The image formed on the means for detection comprises different gray levels, from which information can be derived. Thus, if the object under observation is a human body part, for example, the bones will appear clearly on the image acquired by the means for detection and are distinctly separate from the part formed by the muscles.

Generally, at the time of acquisition of a sequence of radiographic images, there is always a variation in the gray levels found between the successive images of the sequence. In a succession of images acquired the means for detection measures an increase in the variation of the gray level. This phenomenon is due to a persistence or remanence of the radiographic information from one image to the other, which causes the gray level to vary between the images. The variation of the gray level in the sequence depends on the thickness and the composition of the object that is being observed. Thus, for an object observed having a first thickness, will have curve of the variation versus time different than a curve for an object having a second thickness different from the first thickness.

The variation of the gray level is due principally to the trapping of charges in the photodiodes of the means for detection. The variation can also have a number of causes. It can be a question especially of an increase in temperature of the different elements of the apparatus.

In all cases, the variation of the gray levels from one image to another perturbs the measurements acquired by the apparatus. In the case of a large remanence that is, of very considerable variations, the quality and the interpretation of the images acquired may deteriorate considerably. There may be the appearance of a "ghost" or multiple images; that is, superimposing of images acquired previously onto a new image of an object. When the remanence is weaker and does not cause the appearance of ghosts, the measures made are similarly distorted by the spurious variation of the gray level from one image to the other. The variations can be of the same order of magnitude as the dynamics in gray levels of the signal that one wants to detect.

Certain methods enable elimination of this remanence in special applications using special devices. In certain applications, it is possible to determine a law according to which the remanence diminishes over time and to subtract the remanence in the images of the sequence. Consequently, at least one black measurement is made between two acquisition instants corresponding to gray levels supplied by the means for detection in the absence of exposure by radiation. The black measurement enables determining the value of the remanence for that instant. As a result, by virtue of the knowledge of the values of remanence at a given first time the law of decrease of remanence can be deduced. From the law of decrease of remanence between two acquisitions, the value of the remanence at given second time can be deduced of the following acquired image and thus correct the images acquired in a sequence.

This method of correcting sequences of images presumes the use of devices for measuring blacks. Such devices are not always available or accessible on prior art radiographic devices. Consequently, in the majority of cases, it is practically impossible to be able to correct the variation in gray level in a sequence of successive images.

BRIEF DESCRIPTION OF THE INVENTION

An embodiment of the invention provides a method and an apparatus for correction of gray levels in images. An embodiment of the invention is directed to correcting the remanence in a sequence of radiographic images. The method and the apparatus are able to eliminate the utilization of black measurement devices.

An embodiment of the invention provides a method and an apparatus for calibration a device capable of acquiring a sequence of radiographic images. Calibration is done so as to be able to correct the effects of the variation of gray level in a sequence of radiographic images of an object under observation.

An embodiment of the invention provides a method and an apparatus for calibration and correction of radiographic images applicable to all repeatable variation phenomena; that is, variation phenomena that repeat from one measurement of an acquisition sequence to the next when maintaining identical acquisition phenomena from one measurement of an acquisition sequence to the next.

An embodiment of the invention provides a method for calibrating an apparatus capable of acquiring a sequence of radiographic images and correcting images of an object under observation comprising: for each image of a sequence acquired by the apparatus and for a given frequency of acquisition of the sequence, the apparatus is calibrated by determining the value of the variation of a mean of gray levels in at least one zone of interest of the current image of at least one calibration device, the variation being determined relative to the mean gray level of the first image of the sequence in each zone of interest; the determination of the variation is reiterated for a series of images sequences acquired using calibration devices resulting in first images of mean gray levels different from one sequence to another; each image of an image sequence of the object under observation is corrected, comprising zones of observation having different gray levels by subtracting from the current image the variation of one gray level relative to the first image of the object, the subtraction being a function of the gray level considered from each zone of observation.

The invention similarly relates to an apparatus capable of acquiring a sequence of radiographic images implementing a method according to an embodiment of the invention.

BRIEF DESCRIPTION OF THE DRAWINGS

The embodiments of the invention will better understood from the following description, which is purely illustrative and non-limiting, and which should be read with reference to the drawings annexed hereto, wherein.

DETAILED DESCRIPTION OF THE INVENTION

Figure 1:
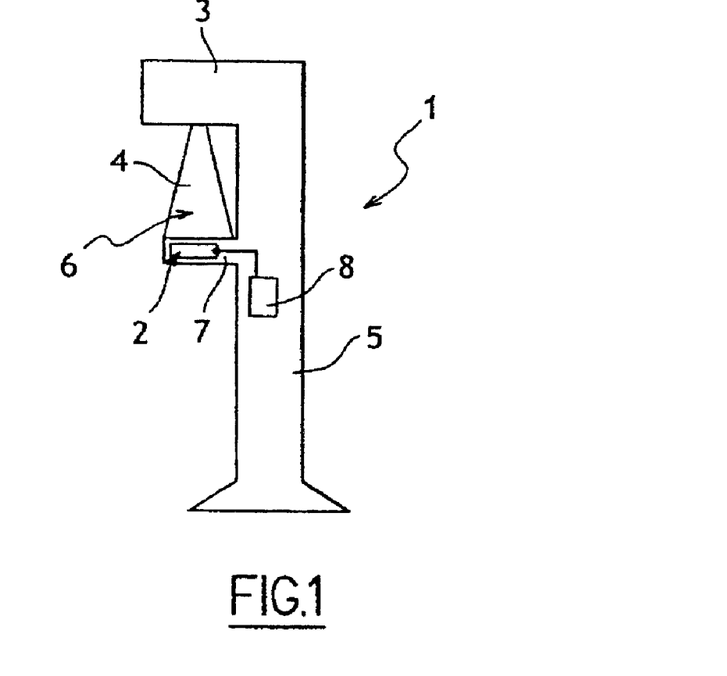
FIG. 1 schematically represents a known apparatus for acquiring a sequence of radiographic images.

An example of a known radiographic apparatus is represented schematically in FIG. 1. In Figure, an apparatus 1 comprises a console 5 (having a substantially vertical extension) and means for providing a radiographic beam emitter 4 facing in the direction of a plate 7 comprising means for detection 2. The means for detection 2 may comprise a photodiode matrix. The means for detection 2 collects the radiation, for example, X-rays, after passing through an object under observation placed in the observation space 6 arranged in the beam 4, between on the one hand the emitter 3 and on the other hand the detector 2 of the apparatus 1. The extensions of the emitter 3 and the detector 2 can be, for example, horizontal and perpendicular to the console 5 but any observation direction is possible, especially due to the fact of the possible rotation of the assembly formed by the emitter 3 and the detector 2 about a substantially horizontal axis of extension. The apparatus 1 may also comprise means for processing 8 enabling acquiring and processing a sequence of images of an object sent from the detector 2.

As noted above, the difference in absorption of the radiation by the different parts of the object under observation enables obtaining information on the composition of the object. In fact, an image formed on the detector 2 comprises different gray levels, from which information can be derived. Thus, if the object under observation is a human body part, for example, the bones will appear clearly on the image acquired by the detector and are distinctly separate from the part formed by the muscles.

Figure 2:
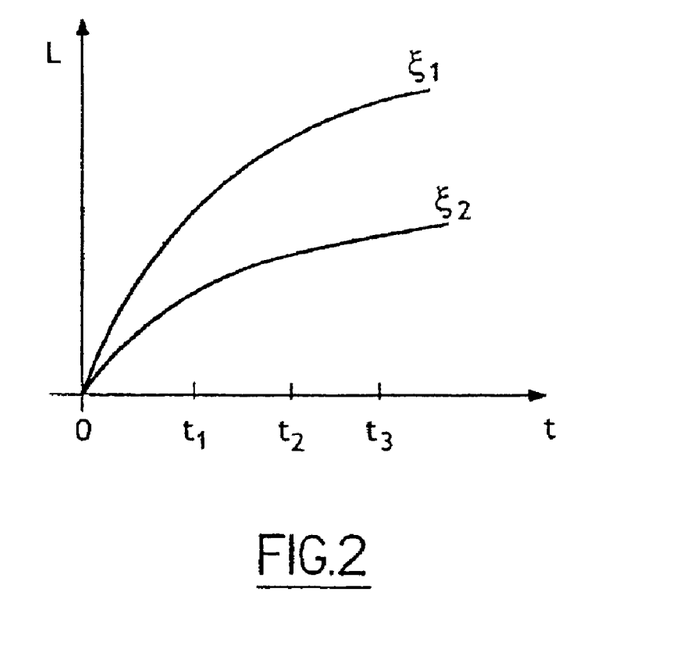
FIG. 2 schematically represents a known development of remanence as a function of time in a sequence of radiographic images.

As noted above, generally, at the time of acquisition of a sequence of radiographic images, there is always a variation in the gray levels found between the successive images of the sequence. Thus, FIG. 2 shows that in a succession of images acquired at times $t_1$, $t_2$, $t_3$, for example, the detector measures an increase in the variation L of the gray level. This phenomenon is due to a persistence or remanence of the radiographic information from one image to the other, which causes the gray level to vary between the images. In the graph of FIG. 2 the variation L of the gray level of the image running at time $t_1$ is represented relative to a first image acquired at time 0. FIG. 2 similarly shows that the variation L of the gray level in the sequence depends on the thickness and the composition of the object that is being observed. Thus, for an object observed having a first thickness, a curve $\xi_1$, while for an object having a second thickness different from the first thickness, a curve $\xi_2$ different from the first.

As noted above, the variation L of the gray level is due principally to the trapping of charges in the photodiodes of the detector. The variation L can also have a number of causes. It can be a question especially of an increase in temperature of the different elements of the device.

As noted above, in all cases, the variation of the gray levels from one image to another perturbs the measurements acquired by the device. In fact, in the case of a large remanence that is, of very considerable variations, the quality and the interpretation of the images acquired may deteriorate considerably. In fact, there may be the appearance of a "ghost" or multiple images; that is, superimposing of images acquired previously onto a new image of an object. When the remanence is weaker and does not cause the appearance of ghosts, the measures made are similarly distorted by the spurious variation of the gray level from one image to the other. The variations can be of the same order of magnitude as the dynamics in gray levels of the signal that one wants to detect.

Figure 3:
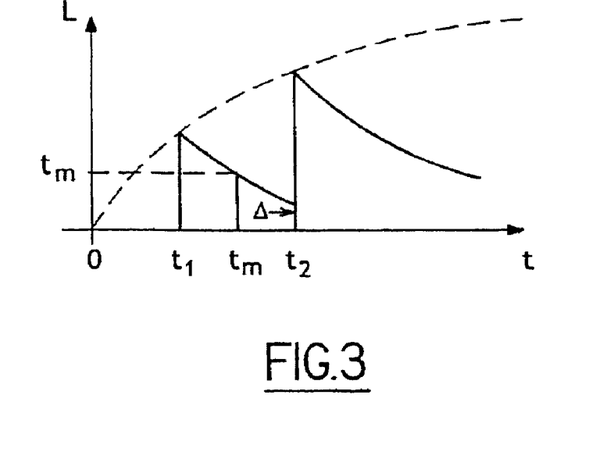
FIG. 3 schematically represents a known correction method for remanence according to the state of technology using a black measurement.

As noted above, in fact, in certain applications, it is possible to determine the law according to which the remanence diminishes over time and to subtract said remanence in the images of the sequence. FIG. 3 shows that between two acquisitions of images done at times $t_1$ and $t_2$, the remanence diminishes according to an exponential distribution that can be determined. Consequently, at least one black measurement is made between two acquisition instants corresponding to gray levels supplied by the detector in the absence of exposure by x-rays. The black measurement is done at time $t_m$, for example, and enables determining the value of the remanence $L_m$ for that instant. As a result, by virtue of the knowledge of the values of remanence at $t_1$, for example, and $t_m$ the law of decrease of remanence can be deduced. From the law of decrease of remanence between two acquisitions, the value of the remanence at time $t_2$ can be deduced of the following acquired image and thus correct the images acquired in a sequence.

An embodiment of the invention is a calibration method of an apparatus capable of acquiring a sequence of radiographic images and correction of images of an object under observation enabling correcting the unwanted effects of the gray level variations in a sequence of radiographic images.

The embodiments of the method can be considered according to two approaches. In a first approach, the calibration step is done prior to acquisition of the sequence of images of the object under observation. The second approach allows performance of the calibration at the same time as acquisition of the images of the object under observation.

In all of the figures, similar elements or steps are referenced using identical numbers.

Figure 4:
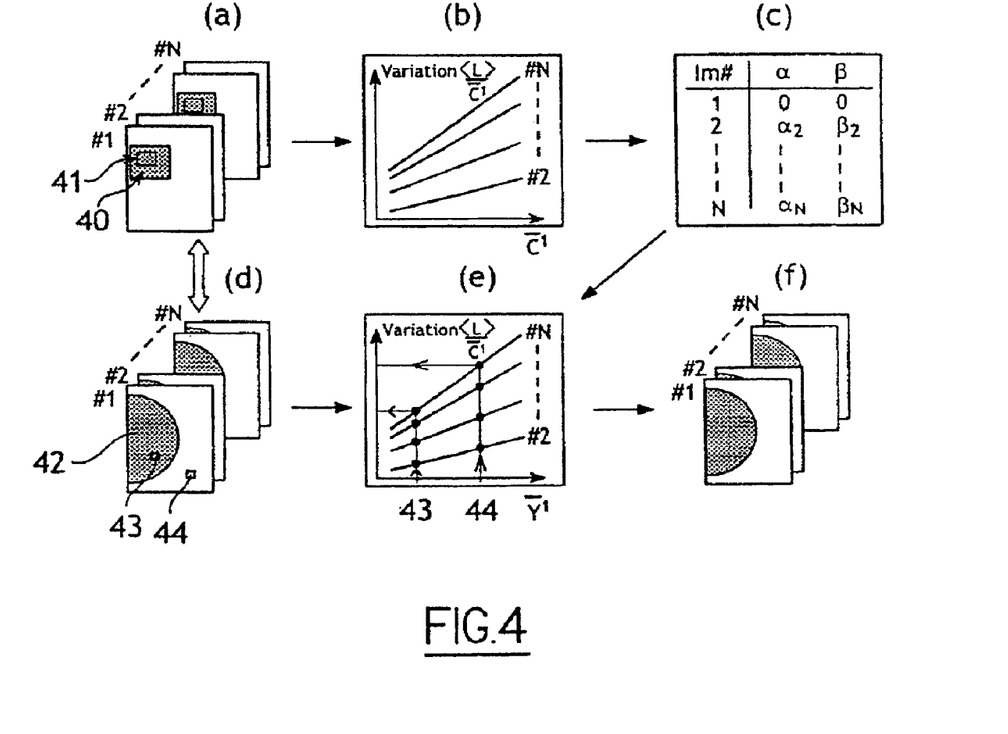
FIG. 4 schematically represents a method of calibration and correction of sequences of image according to an embodiment of the invention, wherein the calibration is done prior to acquisition of the sequence of images of the object under observation.

An embodiment of a method for implementing the first approach is represented schematically in FIG. 4. The method represented in FIG. 4 comprises two parts. A first part is the calibration part comprising three steps (a), (b), (c) in FIG. 4. The second part is the correction of the images of the object under observation. The second part comprises three steps (d), (e) and (f) in FIG. 4.

The calibration part is described as follows. At the time of step (a), using the radiographic apparatus a sequence of images #1, #2, . . . #N are acquired. Acquisition of the sequence is done by observing a calibration device 40. The calibration device 40 is positioned in the zone of observation over the detector of the apparatus and covers the greater part of the detector surface.

This sequence is acquired for a given acquisition frequency. For example, the acquisition frequency can be acquisition of an image every 30 seconds or acquisition of an image every 60 seconds. The images can also be acquired at irregular time intervals. The acquisition frequency of the calibration sequence is preferentially the same as the acquisition frequency that is to be used for acquiring the sequence of images of the object under observation.

FIG. 4(a) thus represents schematically a first sequence of images of at least one calibration device 40 having a given thickness. Each calibration device 40 comprises at least one plate, whose thickness is between 1 cm and 8 cm. Each plate has absorption characteristics for the radiation emitted by the device that are substantially equal to the object that is to be subsequently observed. Thus the known type BR 12 plates as used in mammography, can be utilized since they have the same attenuation characteristics as glandular tissues like the breast. Obviously, for other applications, other materials can be used such as, for example, Lucite or Plexiglas.

At the time of acquisition and for each image a mean gray level is determined on a selected homogeneous zone of interest 41, as shown in FIG. 4(a). The dimensions of the zone of interest 41 are typically 100 pixels×100 pixels. In order to improve the precision of the measurements of the mean gray level in zone 41, acquisition of the images of the calibration device is repeated several times. Thus, typically, each sequence is repeated four to five times. The mean of the results are then determined.

A series of acquisition of sequences is then done using calibration devices 40 having different thicknesses. Thus, the mean gray levels are obtained regarding the zone of interest 41 different between each sequence of the series.

As noted above, the mean gray level evolves as a function of time; that is, it varies between successive images of the same sequence. Thus, the average gray levels in the zone of interest 41 of each image of all the sequences of the series are made. Then, for each $n^{th}$ image $C^{(n)}$ of an sequence acquired by the apparatus and for the zone of interest 41, using means for processing in each apparatus, the value of the mean variation of gray level between the current image and the first image is determined. $L^{(n)}$ records this difference. It is equal to:

$$L^{(n)} = \overline{C^{(n)}} - \overline{C^{(n)}} \quad (1)$$

One then proceeds to the step (b) in FIG. 4. In step (b), for each nth image the relative difference $$L^{(n)} / \overline{C^{(1)}}$$

is determined. Then the graph of $$L^{(n)} / \overline{C^{(1)}}$$

is plotted as a function of $\overline{C^{(1)}}$. Thus, it is confirmed that this function can be approximated by a straight line. The estimated difference $\langle L^{(n)} \rangle$ is thus equal to:

$$\langle L^{(n)} \rangle = \overline{C^{(1)}} \times [\alpha^{(n)} \cdot \overline{C^{(1)}} + \beta^{(n)}] \quad (2)$$

wherein α(n) and β(n) are the coefficients of the linear regression of the curves plotted at the time of step (b) and calculated at the time of a step (c).

Step (c) shows that using the means for processing included in the apparatus, the coefficients of regression $\alpha^{(i)}$ and $\beta^{(i)}$ corresponding respectively to the director coefficients and at the ordinate to the origin of each line of image i is determined. These coefficients are stored in the means for providing a memory of the apparatus included in the means for processing 8 or in means arranged outside of the apparatus. The operation of step (c) ends the calibration.

Each line depends on the one hand on the priority of the $n^{th}$ image in the sequence as indicated by the superscript (n) and, on the other hand, on the frequency of acquisition of the sequence. In other words, and as can be confirmed in FIG. 4(b), for an identical acquisition frequency the curves of image #2 and image #3 are different. This also means that for a different acquisition frequency, the curves of images #2 are different.

The set of curves are plotted corresponding to all of the images of the calibration sequence.

The correction part for the image is described as follows. FIG. 4(d) represents schematically that a sequence of images of an object under observation 42 is acquired with the sequence comprising N images. Without correction, an undesirable variation of the gray level is observed between the successive images of the sequence. Therefore, the calibration data is going to be used for correcting these undesirable variations.

In order to apply a correction to the pixel of coordinates (i, j) of an uncorrected $n^{th}$ image $y^{(n)}$, the mean gray level $\overline{Y_{R(i,j)}}^{(1)}$ is measured in a zone of observation R(i,j) centered on the point (i,j) of the first image, for example, zone 43 in FIG. 4(d). Each zone of observation R(i,j) has a typical size of the order of 25×25 pixels. The size of each zone of observation corresponds substantially to the smallest size of the objects that can be observed such as, for example, a tumor in the field of mammography.

The method for correction is then applied to the image $Y^{(n)}$ by subtracting from the current image the variation of a gray level relative to the first image of the object. FIG. 4(e) shows that by using the determination of the mean gray level $\overline{Y_{R(i,j)}}^{(1)}$ at the time of step (d) and using the calibration data, the value of the variation $\langle L^{(n)} \rangle$ can be reached which is a function of $\overline{Y_{R(i,j)}}^{(1)}$. So, it is sufficient to subtract this value from the value of the current gray level.

A measurement is thus made of the mean gray level in a plurality of zones of observation, for example, similarly in the zone of observation 44 in FIG. 4(*d*). The mean gray level of the zone of observation 44 can be different from the mean gray level of the zone 43.

Mathematically, a corrected $n^{th}$ image $Z_{i,j}^{(1)}$ is obtained using the formula:

$$Z_{i,j}^{(n)} = \lfloor Y_{i,j}^{(n)} - \langle L^{(n)}(\overline{Y_{R(i,j)}}^{(1)}) \rangle \rfloor = \lfloor Y_{i,j}^{(n)} - \overline{Y_{R(i,j)}}^{(1)} \times (\alpha^{(n)} \cdot \overline{Y_{R(i,j)}}^{(1)} + \beta^{(n)}) \rfloor \quad (3)$$

By applying such a correction to the set of images of the sequence, a sequence is obtained, in which all of the variations of gray level have been suppressed or at least reduced.

In the hereinbefore described equations, the measure of the mean level of gray around the pixel (i,j) has been used. A plurality of alternatives is possible as a function of the gray level being considered.

The value of the medial gray level in each zone of observation can also be determined. Thus, the mean gray level is no longer considered. The medial value of a series is the value situated in the middle of the series of values arranged in ascending or descending order.

The use of the median avoids the affect of the measured aberrant gray levels on the value of gray levels taken into account in the correction step. In effect, the extreme values of the series have no influence on the calculation of the median value. Such aberrant values can be measured in the zone of the object 42 having a strong thickness gradient and around an abrupt change in thickness of the object under observation.

The median gray level instead of mean gray level is considered for the object having such thickness gradients. The calibration steps and the equations (1) and (2) remain the same. Equation (3) is slightly modified, because the median gray level is being applied instead of the mean gray level.

The calculation of the median generally slightly increases the processing time of information done in the processing means of the apparatus.

According to second alternative, the mean gray level can also be replaced by the value of $Y_{i,j}^{(1)}$ of gray level of the pixel (i,j). Of course, the value of a zone of interest R(i,j) (43 and/or 44, for example) is no longer averaged and the median value is not calculated.

As for the first alternative, the steps of the method remain the same and only equation (3) is slightly modified, because it is applied to the value $Y_{i,j}^{(1)}$ of the gray level at the pixel (i,j).

The second alternative allows, as did the first alternative, having a good estimation of the variation of gray level in pixels situation near a zone in which the thickness of the object under observation rapidly varies. In contrast to the first alternative, it allows a reduction in the processing time. However, determination of the value of the variation of the gray level is less precise, because there is an enhancement of the quantum noise effect. The effects of quantum noise are significantly reduced by averaging or calculation of the median.

In all of the aforesaid embodiments, it is presumed that the variation of the gray level is homogeneous over the entire surface of the detector of the apparatus. The coefficients $\alpha^{(n)}$ and $\beta^{(n)}$ are determined in fact only in one single zone of interest 41.

An adaptive approach of the first approach is described as follows. The adaptive approach takes into account the inhomogeneity of the variations in gray level over the surface of the detector of the apparatus. It appears that the detectors are not perfect and that there is a disparity of variations of gray level depending on the position on the detector.

Figure 5:
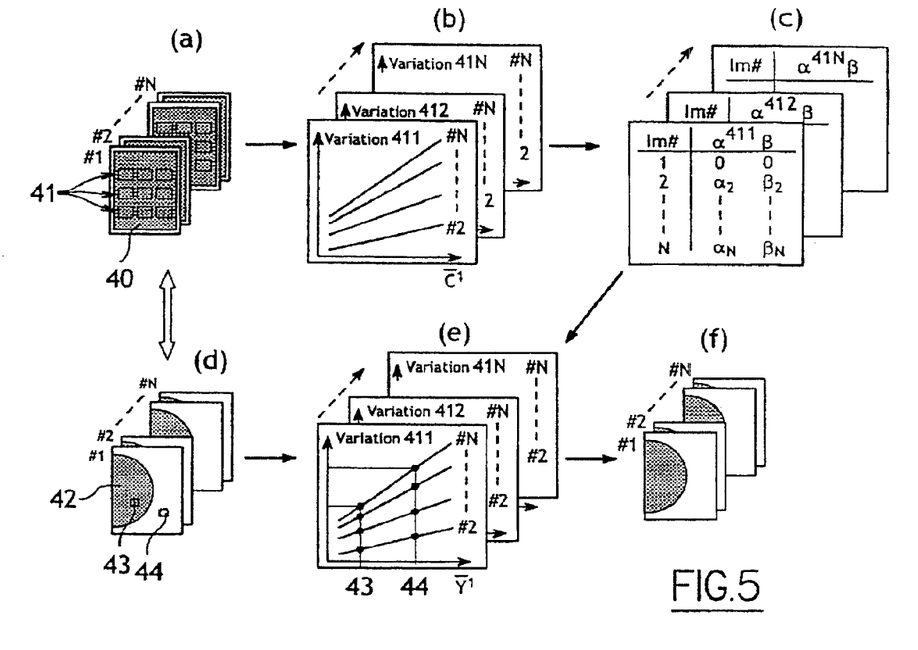
FIG. 5 schematically represents a spatially adaptive embodiment of the method according to FIG. 4.

The steps of an adaptive approach are represented schematically in FIG. 5. The adaptive approach comprises taking into account the inhomogeneity of the variations by performing a calibration on a plurality of zones of interest 41. The zones of interest are regularly divided over the surface of the calibration device and cover a maximum of the surface of the detector.

Thus, at the time of step (a) in FIG. 5, an image sequence of a calibration device 40 disposed over the surface of the detector is acquired. As previously, acquisition of a series of sequences is done, in order to vary the thickness of the calibration device 40. Then, for each image C(n), the remanence $L_\Omega^{(n)}$ is calculated using the equation:

$$L_\Omega^{(n)} = \{L_{k,l}^{(n)} = \overline{C_{k,l}^{(n)}} - \overline{C_{k,l}^{(1)}}\}_{(k,l) \in \Omega}$$

(which is similar to equation (1)), wherein each $R_c(k,l), (k,l) \in \Omega$ represents a zone of interest (41) centered on the pixel having the coordinates (k,l) and where $\Omega$ is the set of pixels on which the zones of interest 41 in FIG. 5 are centered. Similarly, $$L_\Omega^{(n)} / \overline{C^{(1)}}$$

is calculated in that it is plotted as a function of $\overline{C^{(1)}}$.

Thus, at the time of step (b) it is not a graph of a set of straight lines corresponding to the different images that is obtained but a set of graphs, each one corresponding to a zone of interest 41. Thus, one has as many graphs as zones of interest on the surface of the calibration device 40, i.e., a set of graphs 411, 412, . . . 41N corresponding to the set of measurements in the N zones of interest 41.

Step (c) approximates the curves obtained by the straight lines that were defined for each graph, the coefficients $\alpha_\Omega^{(n)}$ and $\beta_\Omega^{(n)}$ henceforth dependent on the zone of interest 41 for which they have been calculated.

At step (d), a sequence of images of an object 42 under observation are acquired. The zones of observation 43 and 44 are determined for which one wishes to effect a correction. Thus the position of the zones of observation is marked relative to the different zones of interest 41.

In step (e) in order to determine the variation of gray level of each zone of observation, the values of $\alpha_\Omega^{(n)}$ and $\beta_\Omega^{(n)}$ are taken, which have been determined for the corresponding zone of interest 41. Then the correction is applied using an equation similar to equation (3). The corrected gray level $Z_{i,j}^{(n)}$ becomes:

$$Z_{i,j}^{(n)} = \lfloor Y_{i,j}^{(n)} - \overline{Y_{R(i,j)}}^{(1)} \times (\alpha_{i,j}^{(n)} \cdot \overline{Y_{R(i,j)}}^{(1)} + \beta_{i,j}^{(n)}) \rfloor$$

(which is similar to formula (3)) wherein $Y_{i,j}^{(n)}$ is the gray level before correction and $\alpha_{i,j}^{(n)}$, $\beta_{i,j}^{(n)}$ are the coefficients determined for each zone of interest and applied to the zone of observation centered on the pixel (i,j). In this fashion, a corrected image $Z_{i,j}^{(n)}$ is obtained in step (f).

Several alternatives of the adaptive approach are possible. A first possible alternative consists of interpolating the $\alpha_{i,j}^{(n)}$ and $\beta_{i,j}^{(n)}$ coefficients of zones of observation arranged outside of the zone of interest. Thus, one could have coefficients and $\alpha_{i,j}^{(n)}$, $\beta_{i,j}^{(n)}$ for any zone of observation. Other alternatives are also possible and utilize the median gray level value or the gray level values on a pixel instead of considering the mean gray level in a zone of observation.

As described above, an embodiment of the method for the first approach considers a calibration before acquiring the image sequence of the object under observation. An embodiment of the method for a second approach does the calibration at the same time as acquisition of the image sequence of the object.

In the second approach of a method according to an embodiment of the invention will now be described the calibration steps take place in the same time as acquisition of the images of the object under observation. The steps of the second approach are represented schematically in FIG. 6.

Figure 6:
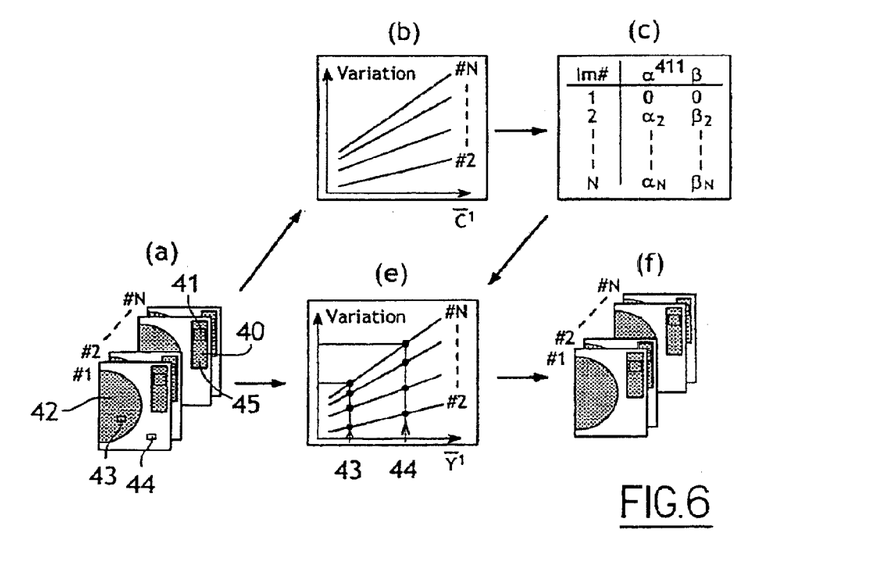
FIG. 6 schematically represents a method according to an embodiment of the invention, wherein the calibration is done at the same time that the acquisition of the sequence of images of the object to be observed.

In FIG. 6(a), the calibration device 40 is placed in a field of acquisition of the apparatus and this is done during acquisition of the sequence of images of the object 42 under observation. By doing so, the necessity of having to do an acquisition series solely for calibration purposes is avoided. However, it was observed that it was desirable as in the first approach to do a series of acquisitions using different thicknesses of the calibration device 40. This thickness variation is desirable to the plotting of the curves of step (b).

Figure 8:
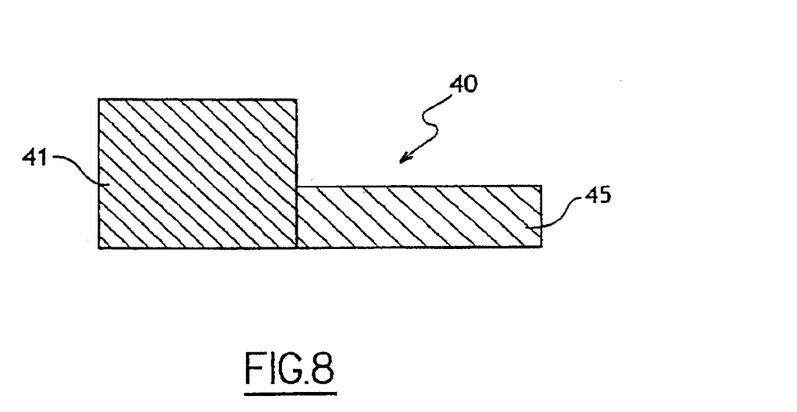
FIG. 8 schematically represents a longitudinal section of a calibration device used in an embodiment of the invention.

In the second approach, the calibration device 40 comprises at least two zones of interest that have mean gray levels that are different from one zone to the other for each image. This is what has been represented in FIG. 8. In FIG. 8, the calibration device 40 comprises a first zone of interest 41 comprising radiation absorption properties different from a second zone 45. The difference in absorption level can be due to a difference in thickness of the device 40 at the level of the two zones 41 and 45 and/or to a difference in the material of the two zones. The device 40 may comprise more than two zones. The greater the number of zones having different properties, the greater will be the number of significant points that the plotting at step (b) of the calibration curves will have. The more precise the plotting of the curves in (b), the more precise their approximation in (c).

Thus, at the time of an identical acquisition of a sequence of images of the calibration device 40, there will be a plurality of points of reference enabling generating the plotting according to FIG. 6(b) similar to that of FIG. 4(b) of the first approach. For each image the more precise the plotting of the curves in (b), the more precise their approximation in (c).

Thus, at the time of an identical acquisition of a sequence of images of the calibration device 40, there will be a plurality of points of reference enabling generating the plotting according to FIG. 6(b) similar to that of FIG. 4(b) of the first approach. For each image $\overline{Y^{(n)}}$ the remanence is calculated using the equation $L^{(n)} = \overline{Y^{(n)}} - \overline{Y^{(1)}}$ (similar to formula (1) already stated).

In step (b) the curves of these relative values are plotted with respect to the mean gray level in the first image as a function of the gray level in the first image.

In step (c) the different curves of the variations of gray level are approximated as a function of the gray level of the first image by the straight lines and the coefficients of the representative function are calculated.

In step (e) the calibration of steps (a), (b), (c) are used. The calibration enables calculation of the variation for each image of the object 42 of the sequence. Thus, in (f), a corrected series of images is obtained.

In an understanding of this approach, the following can be recognized. Firstly, the most precise correction of the gray level variations is obtained. The remanence is determined directly using the images of the sequence of the object under observation. It is then reasonably certain that there are no differences in behavior of the apparatus between the calibration sequences and acquisition of the images of the object under observation. Secondly, it is generally not necessary to do an entire series of measurements in order to obtain the calibration curves. The calibration is done directly, at the same time as acquisition of the images of the object under observation. Thus, there is a considerable time savings for the operator of the apparatus.

It is not easy to apply an adaptive approach to the second approach: the presence of the object under observation, calibration of the entirety of the acquisition field cannot be done. Thus, according to a first alternative of the second approach, a spatial model is used in order to take into account any disparities of variation of gray level as a function of the position on the detector. The steps of such a variant are represented schematically in FIG. 7.

Figure 7:
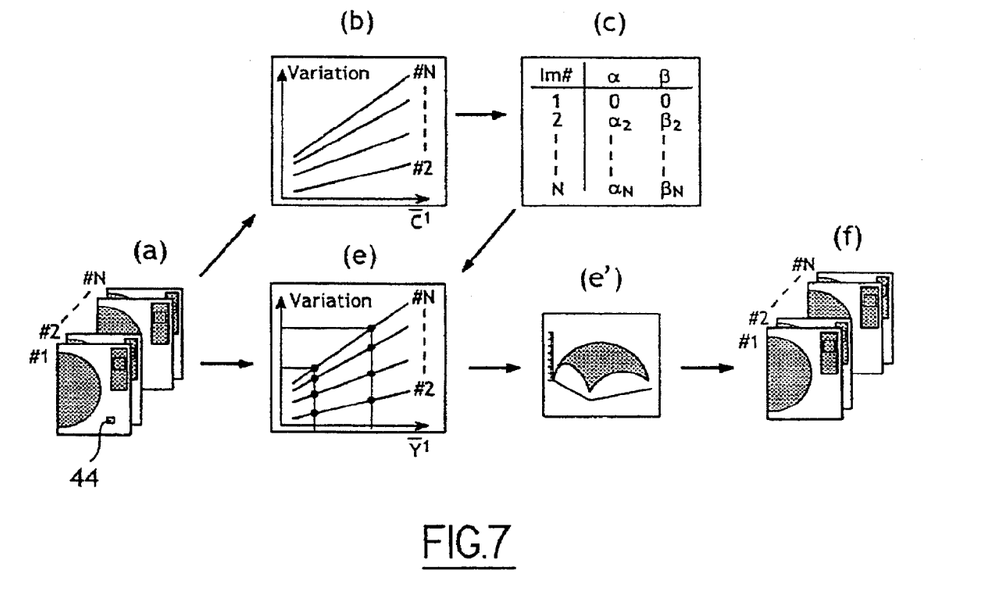
FIG. 7 schematically represents a spatially adaptive embodiment of the method according to FIG. 6.

Steps (a), (b), (c) and (e) remain the same as those of FIG. 6. However, between step (e) and step (f) a step (e') is added allowing application of a spatial model of the disparities of the variations.

Thus, in order to apply a correction to a pixel (i,j) of image Y(n), the mean gray level $\overline{Y_{R(i,j)}}^{(1)}$ is measured in a zone of observation 44, for example, centered around the point (i,j). After calibration, the gray level $Z_{i,j}^{(n)}$ of the pixel (i,j) becomes:

$$Z_{i,j}^{(n)} = \lfloor Y_{i,j}^{(n)} - \lambda_{i,j} \times \langle L^{(n)}(\overline{Y_{R(i,j)}}^{(1)}) \rangle \rfloor = \lfloor Y_{i,j}^{(n)} - \lambda_{i,j} \times \overline{Y_{R(i,j)}}^{(1)} \times (\alpha^{(n)} \cdot \overline{Y_{R(i,j)}}^{(1)} + \beta^{(n)}) \rfloor$$

(which is similar to formula (3)), wherein $Y_{i,j}^{(n)}$ is the gray level before calibration $\alpha^{(n)}$ and $\beta^{(n)}$ are the linear regression coefficients of approximation of the variation of gray level and $\lambda_{i,j}$ is a measured or modeled gain factor for the pixel (i,j).

In order to obtain a measured $\lambda_{i,j}$ gain factor one can, for example, utilize a calibration for a plurality of zones of interest as in the adaptive approach described for the first approach. The different values of $\lambda_{i,j}$ will be thus entered in the processing means of the apparatus and applied at the time of the correction step.

In order to model the $\lambda_{i,j}$ gain factor, one can utilize the inverse of the apparatus gain factor. The $K_{i,j}$ gain factor of the apparatus compensates the inhomogeneity of illumination of the detector by the emitter and the inhomogeneity of the response of the photodiodes of the detector.

In this fashion, an image corrected in gain is observed on the detector of the form: $K_{i,j}$ (Im+remanence), wherein Im is the image of the object uncorrected in gain and inhomogeneous. The part ($K_{i,j}$ Im) is a homogenous image. Thus, the inhomogeneous remanence that is observed on the detector is: ($K_{i,j}$ remanence). The inhomogeneity of the remanence observed is due to the $K_{i,j}$ gain factor. Thus, in order to find a homogeneous remanence, the $\lambda_{i,j}$ factor is applied to the term ($K_{i,j}$ remanence), such that:

$$\lambda_{i,j} = 1/K_{i,j}.$$

It is the homogeneous remanence obtained after this multiplication that can be subtracted from the current image.

According to a second possible alternative of the second approach, one compensates for the fact that few of the values for the plotting of the calibration curve can be acquired. As the calibration data are acquired in the same time as the image observation data, there is only one variation value per image for a given gray level.

Figure 9:
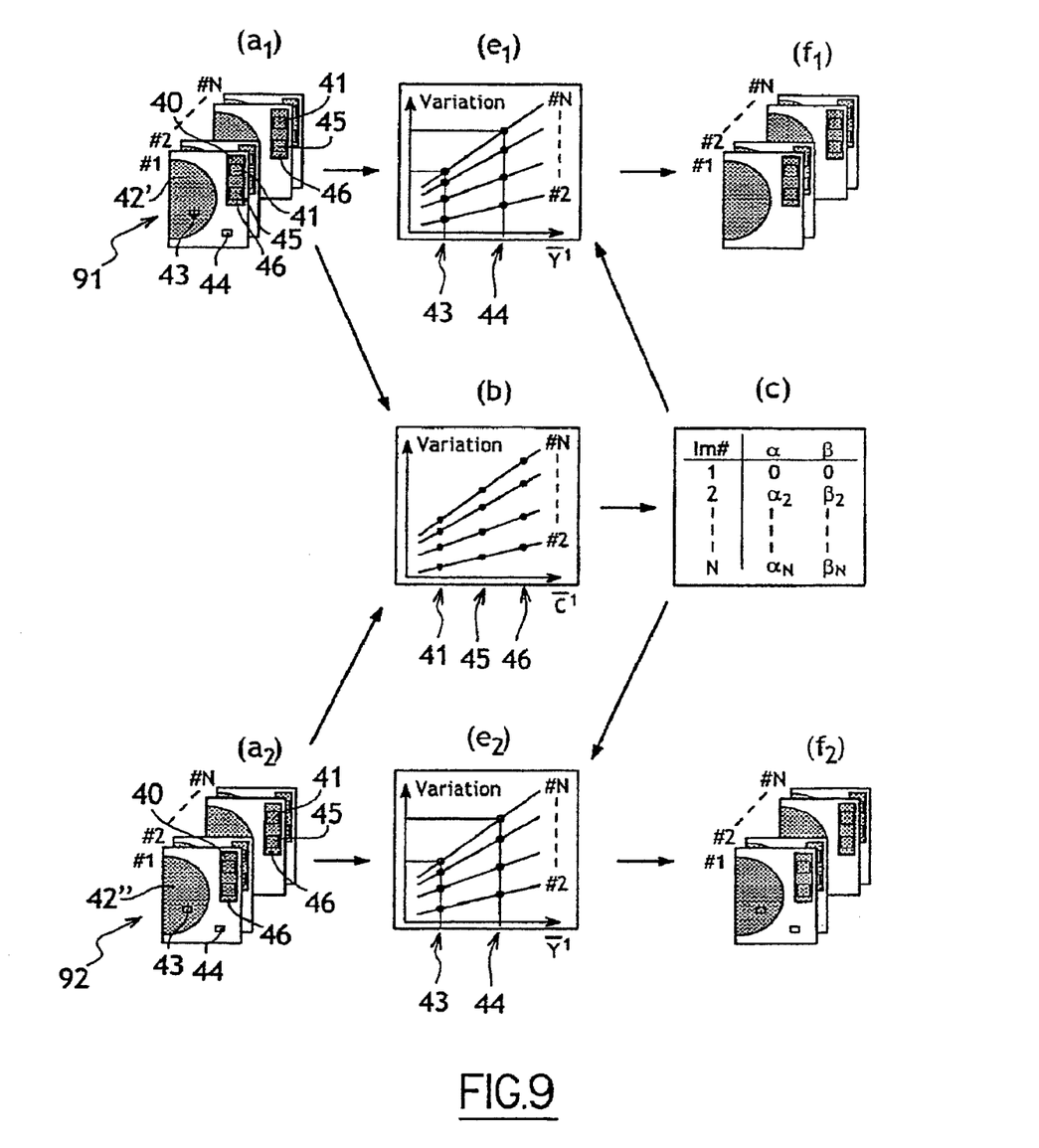
FIG. 9 schematically represents the different steps of an embodiment of the invention wherein calibration data of at least two successive sequences are combined.

In order to increase the number of measurement points for improving the precision of the calculation of the regression coefficients $\alpha^{(i)}$ and $\beta^{(i)}$ of the approximation, it is possible to combine the information from a plurality of successive acquisition sequences of different objects under observation. FIG. 9 represents schematically the different steps of this alternative. It can be seen in FIG. 9 that at least two object images 42' and 42" are acquired at the in these steps (referenced by ($a_1$) and ($a_2$)). The two sequences 91 and 92 are both acquired in under the same conditions of acquisition but successively. For example, the sequence 91 is acquired before sequence 92. The sequence 91 has, in particular, the same acquisition frequency as sequence 92. In step (b), the measurements collected over the calibration device 40 in each of the two sequences 91 and 92 are combined in order to increase the number of points, regarding which the regression coefficients are calculated in step (c). In FIG. 9, the device 40 comprises three zones of interest 41, 45 and 46. FIG. 9(b) represents the different points issuing from each sequence for each image for the zones 41, 45 and 46. In this fashion, the number of points is doubled, if the two sequences are combined. The precision of the approximations is thus increased. The two sequences 91 and 92 are then corrected in steps ($e_1$) and ($e_2$), respectively. The correction utilizes the regression coefficients calculated in step (c). Thus, in ($f_1$) and ($f_2$) corrected images are obtained.

The alternative of FIG. 9 can be generalized to as many sequences as may be desired. For each image, there is a cluster of points for each gray level. Furthermore, the alternative of FIG. 9 can be iterative; that is, for each new sequence acquired new regression coefficients can be recalculated.

Figure 10:
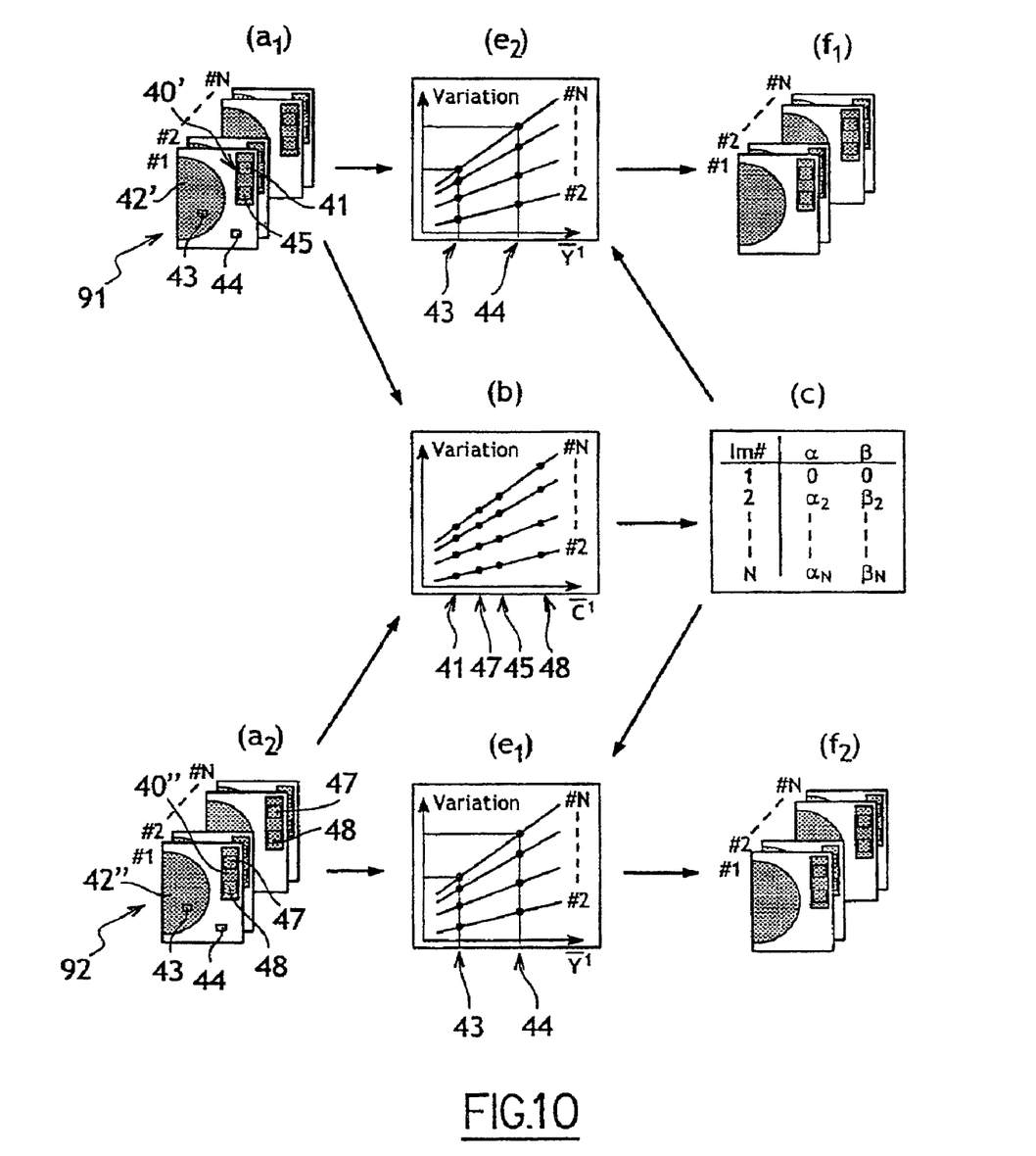
FIG. 10 schematically represents the different steps of an embodiment of the invention wherein calibration data of at least two sequences having different calibration devices are combined.

Another alternative of the second approach compensates for the fact that few functional points are available for the plotting of the calibration curves. Actually, due to the fact of the presence of the object under observation in the acquisition field of the detector, calibration devices of larger dimensions cannot be arranged in the field. Consequently, the devices no not have a large number of different zones of attenuation characteristics. The present variant utilizes different calibration devices from one sequence to another in order to augment the number of functional points. The steps of such an alternative are represented schematically in FIG. 10. In FIG. 10 at least two sequences of images of the object 42' and 42" are acquired in the steps ($a_1$) and ($a_2$). The two sequences 91 and 92 are both acquired under the same conditions of acquisition, successively. The sequence 91, especially, has the same acquisition frequency as the sequence 92. The calibration devices 40' and 40" used in the two sequences are, in contrast, different from one sequence to another. For example, the device 40' has two zones of interest 41 and 45, while the device 40" has at least one, preferably two zones of interest 47 and 48. The zones 47 and 48 have radiation attenuation characteristics different from that of zones 41 and 45. In step (b), the measurements collected using the calibration devices 40' and 40" in each of the two sequences 91 and 92 are combined in order to increase the number of functional points, using which the regression coefficients of step (c) are calculated. The measurement points of zones 47 and 48 at the time of acquisition of the sequence 92 complements the points of zones 41 and 45 acquired during the acquisition of sequence 91. For example, the two devices 40' and 40" are alternatively arranged on the detector at the time of successive acquisitions of two different objects 42' and 42".

In the alternatives of FIGS. 9 and 10 a spatial model can, of course, be used.

Other variants of the second approach are also possible and they utilize gray level median values or the gray level values on a pixel, instead of considering the mean gray level in a zone of observation.

The introduction of the gain factor $\lambda_{i,j}$ during the correction step can be similarly applied to the first approach.

In the developments of the above, the relative estimated value $\langle L^{(n)} \rangle / \overline{C^{(1)}}$ in the $n^{th}$ image in function of the mean gray level in the first image $\overline{C^{(1)}}$ can be approximated by a straight line. Of course, in the above developments, the visible graphic representation of FIG. 4(b), for example, by other functions, whose characteristics can be determined or are known. The approximation function chosen depends on the repeatable phenomenon that is observed as well as the precision that one wishes to obtain at the time of calibration. The approximation function can thus, for example, be a polynomial function comprising the powers of $\overline{C^{(1)}}$ or an exponential function.

The embodiments of the invention is therefore complemented by the following features, taken singly or in any technically possible combination thereof: a graphical representation is approximated having respectively as its ordinate and abscissa; the ratio having in the numerator the mean gray level variation of the current image of the sequence of the calibration device relative to the mean gray level of the first image and in the denominator the mean gray level of the first image, and the different mean gray levels of each first image; a function for which the characteristics are known; the function is a straight line; the gray level that is corrected in each zone of each image of the object under observation is the mean gray level; the gray level that is corrected in each zone of each image of the object under observation is the median gray level; the gray level of at least one selected pixel in each image of the object under observation is corrected; the calibration takes place before the acquisition of the sequence of images of the object under observation; each mean gray level value of the series of sequences of the calibration is given by the observation of at least one calibration plate of defined thickness constituting each calibration device, its thickness change from one series to the other; the average gray level is determined on a plurality of zones of interest simultaneously at the time of calibration; the subtraction at the time of the correction step depends on the one hand on the position of the zone of observation relative to each zone of interest; the value subtracted from each image of the sequence of images of the object is a function on the one hand of the position of the zone of observation and on the other hand a function of the defined spatial gain; the calibration takes place during the acquisition of the sequence of images of the object under observation; each calibration device is placed in a field of acquisition of the apparatus comprising also the object under observation; each calibration device comprises at least two zones of interest having a mean gray level different from one zone to another for each image; the value subtracted from each image of the sequence of images of the object is a function on the one hand of the position of the zone of observation and on the other of the function of the spatial gain of the apparatus; the calibration measurements of at least two acquisitions of successive sequences are combined, and the calibration measurements of at least two acquisitions of successive sequences having different calibration devices are combined.

One skilled in the art may propose or make various modifications to the way/structure and/or function and/or result and/or steps of the disclosed embodiments without departing from the scope and extant of protection.

We claim:

1. A method for correcting an image of an object under observation, comprising:
   obtaining a first sequence of images of a calibration device utilizing an apparatus;
   determining a first mean gray level in a zone of interest in a first image in the first sequence of images;
   determining a second mean gray level in a zone of interest in a second image in the first sequence of images;
   determining a variation value corresponding to a variation between the first mean gray level and the second mean gray level;
   obtaining a second sequence of images of the object utilizing the apparatus;
   determining a third mean gray level in a zone of interest in a third image in the second sequence of images; and
   correcting a fourth image of the object in the second sequence of images based on the variation value and the third mean gray level to obtain a corrected fourth image of the object.

2. The method of claim 1, wherein correcting the fourth image of the object in the second sequence of images based on the variation value and the third mean gray level to obtain the corrected fourth image of the object comprises:
   multiplying the variation value and the third mean gray level to obtain a first value; and
   subtracting the first value from the fourth image to obtain the corrected fourth image.

3. The method of claim 1, wherein correcting the fourth image of the object in the second sequence of images based on the variation value and the third mean gray level to obtain the corrected fourth image of the object comprises:
   multiplying the variation value and the third mean gray level to obtain a first value;
   multiplying the first value and a spatial gain factor to obtain a second value; and
   subtracting the second value from the fourth image to obtain the corrected fourth image.

4. The method of claim 1, wherein the calibration device is placed in a field of acquisition of the apparatus.

5. The method of claim 1, wherein the calibration device comprises at least first and second zones of interest having first and second mean gray levels, respectively.

6. An apparatus for correcting an image of an object under observation, comprising:
   an x-ray detector configured to obtain a first sequence of images of a calibration device;
   a processor configured to determine a first mean gray level in a zone of interest in a first image in the first sequence of images;
   the processor further configured to determine a second mean gray level in a zone of interest in a second image in the first sequence of images;
   the processor further configured to determine a variation value corresponding to a variation between the first mean gray level and the second mean gray level;
   the processor further configured to obtain a second sequence of images of the object;
   the processor further configured to determine a third mean gray level in a zone of interest in a third image in the second sequence of images; and
   the processor further configured to correct a fourth image of the object in the second sequence of images based on the variation value and the third mean gray level to obtain a corrected fourth image of the object.

7. The apparatus of claim 6, wherein the processor is further configured to multiply the variation value and the third mean gray level to obtain a first value, the processor further configured to subtract the first value from the fourth image to obtain the corrected fourth image.

8. The apparatus of claim 6, wherein the processor is further configured to multiply the variation value and the third mean gray level to obtain a first value, the processor further configured to multiply the first value and a spatial gain factor to obtain a second value, the processor further configured to subtract the second value from the fourth image to obtain the corrected fourth image.

9. The apparatus of claim 6, wherein the calibration device is placed in a field of acquisition of the x-ray detector.

10. The apparatus of claim 6, wherein the calibration device comprises at least first and second zones of interest having first and second mean gray levels, respectively.

* * * * *